(12) United States Patent
Bech-Hansen

(10) Patent No.: US 6,875,585 B2
(45) Date of Patent: Apr. 5, 2005

(54) GPI-ANCHORED SMALL LEUCINE-RICH PROTEOGLYCAN GENE NYX

(76) Inventor: N. Torben Bech-Hansen, 526 - 37 Street N.W., Calgary AB (CA), T2N 3B8

( * ) Notice: Subject to any disclaimer, the term of this patent is extended or adjusted under 35 U.S.C. 154(b) by 65 days.

(21) Appl. No.: 09/853,753

(22) Filed: May 14, 2001

(65) Prior Publication Data

US 2002/0182669 A1 Dec. 5, 2002

(30) Foreign Application Priority Data

May 12, 2000 (CA) .............................................. 2306241

(51) Int. Cl.⁷ .......................... C12P 21/06; C12N 15/00; C07H 21/02; C07H 21/04; C07K 1/00
(52) U.S. Cl. .................. 435/69.1; 435/320.1; 536/23.1; 536/23.5; 530/350
(58) Field of Search ............................. 435/69.1, 320.1; 536/23.1, 23.5; 530/350

(56) References Cited

PUBLICATIONS

Yan et al., 2000, Science, 290, pp. 523–527.*
Introduction to proteins and protein engineering, 1986, Elsevier, p. 41.*

Loss of Function Mutations in a Calcium–Channel$\alpha_1$ subunit gene in Xp11.23 cause incomplete X–linked congenital stationary Night blindness—Paper by Bach–Hansen, et al. Jul., 1996.

Mutations in NYX, encoding the leucine–rich proteoglycan nyctalopin, cause X–linked incomplete cogenital stationary night blindness—Paper by Bech–Hansen et al. Nov., 2000.

Evidence for Genetic Heterogeneity in X–linked Cogenital Stationary Night Blindness—Paper by Bech–Hansen, et al.—published Apr. 7, 1998.

Leucine–Rich Repeat Glycoproteins of the Extracellular Matrix—Paper by Hocking, et al. accepted Jan. 29, 1998.

* cited by examiner

*Primary Examiner*—John Ulm
*Assistant Examiner*—Olga N. Chernyshev
(74) *Attorney, Agent, or Firm*—Bennett Jones LLP

(57) ABSTRACT

A mammalian gene (NYX) which encodes a GPI-anchored small leucine-rich proteoglycan, nyctalopin, together with compositions and methods involving NYX and nyctalopin or homologous molecules. Mutations in NYX may cause complete X-linked congenital stationary night blindness in humans.

6 Claims, 9 Drawing Sheets

FIGURE 1A
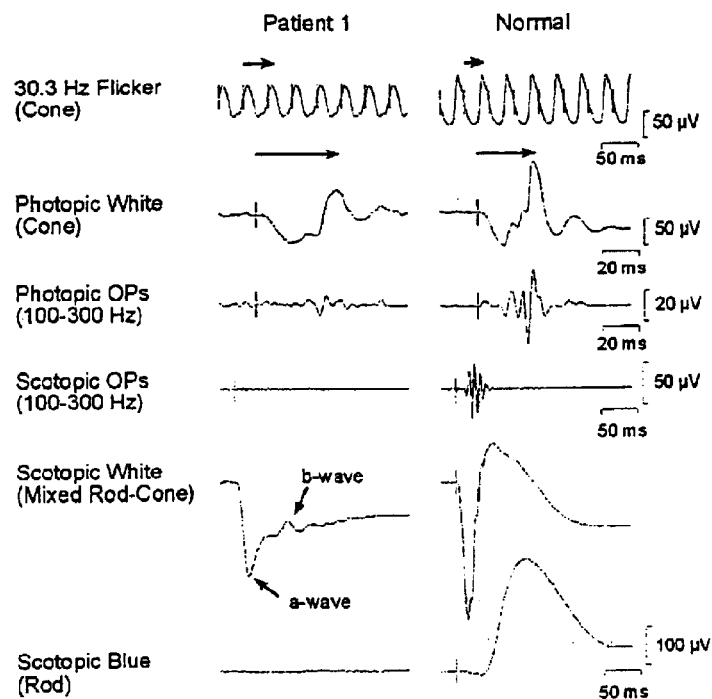
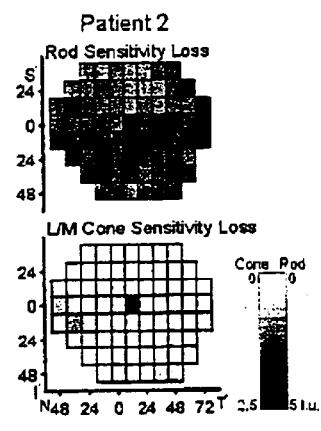
FIGURE 1B
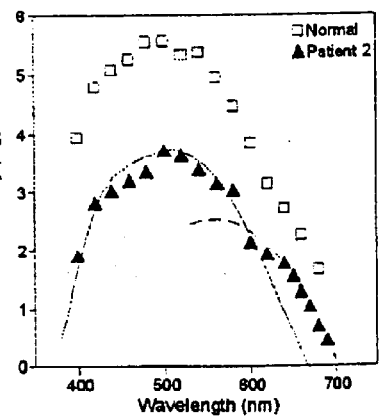
FIGURE 1C

+Leucine-rich repeats and the distribution of mutations in the Nyctalopin protein

```
                        V
MKGRGMLVLLLHAVVLGLPSAWAVGACARACPAACACSTVERGCSVRCDR      - 50
                               del
```

| | | |
|---|---|---|
| 1. | AGLLRVPAELPCEAVSIDLDRNGL | - 74 |
| 2. | RFLGERAFGTLPSLRRLSLRHNNL | - 98 |
| 3. | SFITPGAFKGLPRLAELRLAHNGDL | - 123 |
| 4. | RYLHARTFAALSRLRRLDLAACRL | - 147 |
| 5. | FSVPERLLAELPALRELAAFDNLFRRVPGALRGL | - 181 |
| 6. | ANLTHAHL15LRRLRSLSLQANRV | - 218 |

```
        ERGRIEAVASSSLQG
                      ^
```

| | | |
|---|---|---|
| 7. | RAVHAGAFGDCGVLEHLLLNDNLL | - 242 |
| 8. | AELPADAFRGLRRLRTLNLGGNAL | - 266 |
| 9. | DRVARAWFADLAELELLYLDRNSI | - 290 |
| 10. | AFVEEGAFQNLSGLLALHLNGNRL | - 314 |
| 11. | TVLAWVAFQPGFFLGRLFLFRNPW | - 338 |

β – sheet    α – helix

```
                        |
CCDCRLEWLRDWMEGSGRVTDVPCASPGSVAGLDLSQVTFGRSSDGLCVD      - 388
PEELNLTTSSPGPSPEPAATTVSRFSSLLSKLLAPRVPVEEAANTTGGLA      - 438
NASLSDSLSSRGVGGAGRQPWFLLASCLLPSVAQHVVFGLQMD            - 481
```

^ insertions of SVPERLL, GLR and RLR, respectively
v most likely signal peptide cleavage site

FIGURE 3B [SEQ ID. NO:2]

FIGURE 4A
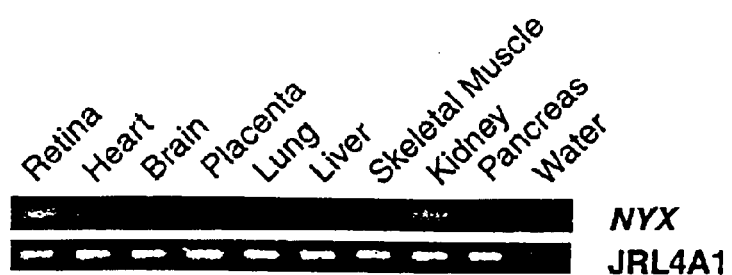
FIGURE 4B  FIGURE 4C  FIGURE 4D
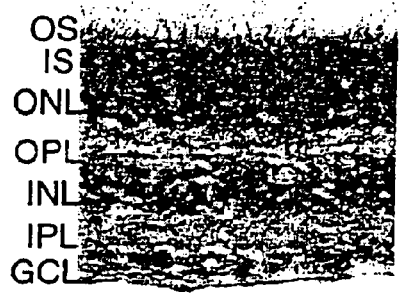 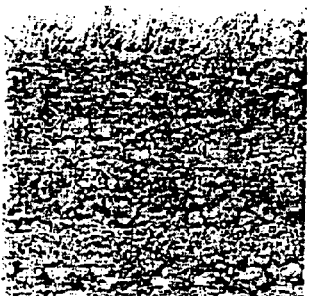 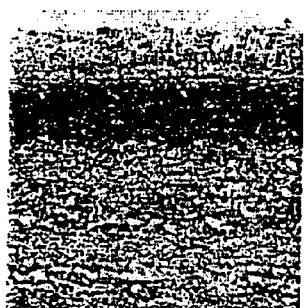
NYX-AS    NYX-S     RHO-AS FIGURE 5A
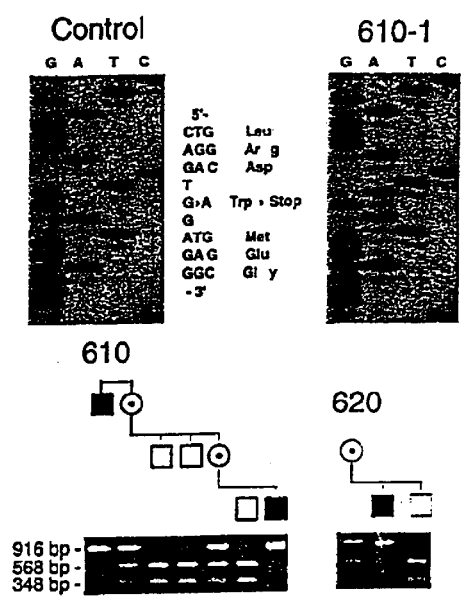
FIGURE 5B
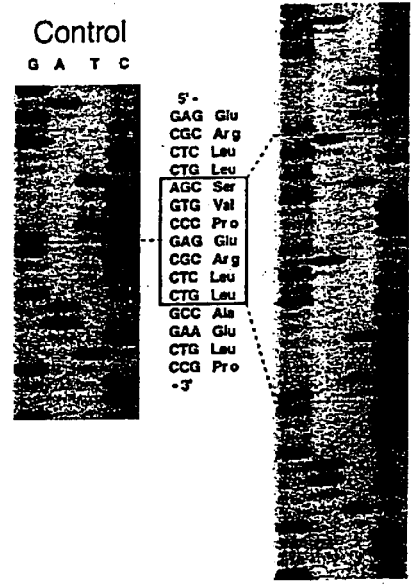
FIGURE 5C
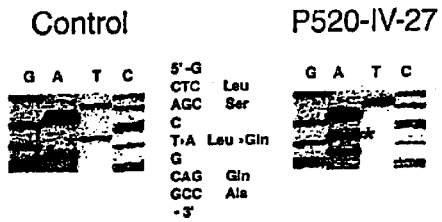
FIGURE 5D Table 1 • Nyctalopin mutations in families with complete CSNB

| Family[a] | Origin | Mutation[b] | Codon change | Predicted effect on nyctalopin |
|---|---|---|---|---|
| 290,740,830,Y1,Y2,Y3,R5[c] | USA | 85-108del24nt[d] | RACPAACA29-36del | partial loss of N-terminal cysteine cluster |
| P23,340 (2) (ref 13) | Netherlands | 452C>T | P151L | missense, proline to leucine |
| 650 (2) | Canada | 464^465ins21nt | SVPERLL155-156ins | expansion of LRR5[e] |
| 750[f] (1),780 (1) | Canada,USA | 551T>C | L184P | missense, leucine to proline |
| 540 (6)(ref 28, family 2) | Germany | 556-618del50ins3nt | | frameshift with stop at codon 259 |
| 640 (2) | USA | 619^620ins9nt | LLR207-208ins | expansion of LRR6 |
| R7 (7) | USA | 628^629ins9nt | CLR209-210ins | expansion of LRR6 |
| P520 (2) | Netherlands | 638T>A | L213Q | missense, leucine to glutamine |
| 580 (2) | Canada | 647A>G | N216S | missense, asparagine to serine |
| 550 (9)(ref 28, family 3) | Germany | 695T>C | L232P | missense, leucine to proline |
| B1 (3) | USA | 792C>G | N264K | missense, asparagine to lysine |
| B660 (1) | USA | 854T>C | L285P | missense, leucine to proline |
| B2 (5) | USA | 893T>C | F298S | missense, phenylalanine to serine |
| 610, 620 (4,10) | Costa Rica | 1049G>A | W350X | protein truncation, loss of GPI-anchoring |

[a] families Y1, Y2, Y3, R5, R7, B1 and B2 were first reported in reference 25. Earlier reports on other families is indicated following the family designation.
[b] following the recommendations of Nomenclature Working Group.
[c] number of affected males in these families: 8, 1, 4, 8, 2 and 5, respectively. For all other families in this table this information is shown in first set of parentheses following the family designation.
[d] in the analysis of X chromosomes with this deletion, we observed identical haplotypes across Xp11.4 from DXS556 to DXS228 with some chromosomes diverging proximally or distally beyond this region (15 markers tested)
[e] LRR, leucine-rich repeat.
[f] Patient 1, whose electrophysiological results are shown in Fig. 1.

SEQUENCE LISTING

```
<160> NUMBER OF SEQ ID NOS: 14

<210> SEQ ID NO 1
<211> LENGTH: 2297
<212> TYPE: DNA
<213> ORGANISM: Mus sp.
<300> PUBLICATION INFORMATION:
```

```
<301> AUTHORS: Bech-Hansen NT et al.
<302> TITLE: Mutations in NYX, encoding the leucine-rich proteoglycan
      nyctalopin, cause X-linked complete congenital stationary night
      blindness
<303> JOURNAL: Nature Genetics
<304> VOLUME: 26
<305> ISSUE: 3
<306> PAGES: 319-323
<307> DATE: 2000-11-01
<308> DATABASE ACCESSION NUMBER: GenBank / AF254868
<309> DATABASE ENTRY DATE: 2000-12-23

<400> SEQUENCE: 1
ggctgaggga gtggaggggg acctcagagg agcaggacca gggagactcc caggacggta     60
ggggtcccac ggctgggtgg tcctaagcca ctgggtggat gaaaggccga gggatgttgg    120
tcctgcttct gcatgcggtg gtcctcggcc tgcccagcgc ctgggccgtg ggggcctgcg    180 ccgcgcttg tcccgccgcc tgcgcctgca gcaccgtgga gcgcggctgc tcggtgcgct    240
gcgaccgcgc gggcctcctg cgggtgccgg ccgagctccc gtgcgaggcg gtctccatcg    300
acctggaccg gaacggcctg cgcttcctgg gcgagcgagc cttcggcacg ctgccgtcct    360
tgcgccgcct gtcgctgcgc cacaacaacc tgtccttcat cacgcccggc gccttcaagg    420
gcctgccgcg cctggctgag ctgcgcctgg cgcacaacgg cgacctgcgc tacctgcacg    480
cgcgcacctt cgcggcgctc agccgcctgc gccgcctaga cctagcagcc tgccgcctct    540
tcagcgtgcc cgagcgcctc ctggccgaac tgccggccct gcgcgaactc gccgccttcg    600
acaacctgtt ccgccgcgtg ccgggcgcgc tgcgcggcct ggccaacctg acgcacgcgc    660
acctggagcg cggccgcatc gaggcggtgg cctccagctc gctgcagggc ctgcgccgcc    720
tgcgctcgct cagcctgcag gccaaccgcg tccgtgccgt gcacgctggc gccttcgggg    780
actgtggcgt cctggagcat ctgctgctca cgacaacct gctggccgag ctcccggccg    840
acgccttccg cggcctgcgg cgcctgcgca cgctcaacct gggtggcaac gcgctggacc    900
gcgtggcgcg cgcctggttc gctgacctgg ccgagctcga gctgctctac ctggaccgca    960
acagcatcgc cttcgtggag gagggcgcct tccagaacct ctcgggtctc ctcgcgctgc   1020
acctcaacgg caaccgcctc accgtgctcg cctgggtcgc cttccagccc ggcttcttcc   1080
tgggccgcct cttcctcttc cgcaacccgt ggtgctgcga ctgccgtctg gagtggctga   1140
gggactggat ggagggctcc ggacgtgtca ccgacgtgcc gtgcgcctcc ccgggctccg   1200
tggccggcct ggacctcagc caggtgacct cgggcgctc ctccgatggc ctctgtgtgg    1260
accccgagga gctgaacctc accacgtcca gtccaggccc gtccccagaa ccagcggcca   1320
ccaccgtgag caggttcagc agcctcctct ccaagctgct ggccccgagg gtcccggtgg   1380
aggaggcggc caacaccact gggggctgg ccaacgcctc cctgtccgac agcctctcct    1440
cccgtggggt gggaggcgcg ggccggcagc cctggtttct cctcgcctct tgtctcctgc   1500
ccagcgtggc ccagcacgtg gtgtttggcc tgcagatgga ctgacctggc cagagggggg   1560
aaagtttgct taactgggct tgagtgtgtt tgtggtaagg ggagaggagc cggaatggag   1620
ggcagaggtg aaaatcccag tggagggtgg aaggaaccgt ttgcctccag agatggcccc   1680
agggagaaca cagggacgtg ccactcgagg gggaggatgg tatggatttc tgcttttgtc   1740
acacgggcat ccattggaaa agagaagcaa gaatgaacgt gggccctcgg gtgggaagac   1800
taggaatcgg aagcttctag ggcttcacat cccttcccct ccctcccct tccctcatc    1860 ttccaggcaa cagtgcctgc aaggcctgaa ttagagagac ttccattggc taagtagtta   1920
agagccgtcc catttctcct ggcggggtaa cccattacac cgaagtcctt tgttttctac   1980
```

-continued

```
cacaatcctc ctcctcctct ccagggcct ggaaacacta ggattcagga aggtaggcag    2040
gacgtgagag aagggagatg ggagagagat ttaagacaaa gggtggcggt ggttcctggg    2100
gtctgagatg tgttaggagg cgtttaaaac aaagatccag ttcatttact ccacagttat    2160
tcccagggct ggccctagcc acaaaggaac tttagggcag ggtagggaaa aaggggcag     2220 caggggtgt gtttgtggac aaataaattt gtaaagtccg aggattaaaa aaaaaaaag      2280 gttaaaccgg tttctct                                                   2297
```

<210> SEQ ID NO 2
<211> LENGTH: 481
<212> TYPE: PRT
<213> ORGANISM: Mus sp.

<400> SEQUENCE: 2

```
Met Lys Gly Arg Gly Met Leu Val Leu Leu His Ala Val Val Leu
1               5                   10                  15

Gly Leu Pro Ser Ala Trp Ala Val Gly Ala Cys Ala Arg Ala Cys Pro
            20                  25                  30

Ala Ala Cys Ala Cys Ser Thr Val Glu Arg Gly Cys Ser Val Arg Cys
        35                  40                  45

Asp Arg Ala Gly Leu Leu Arg Val Pro Ala Glu Leu Pro Cys Glu Ala
    50                  55                  60

Val Ser Ile Asp Leu Asp Arg Asn Gly Leu Arg Phe Leu Gly Glu Arg
65                  70                  75                  80

Ala Phe Gly Thr Leu Pro Ser Leu Arg Arg Leu Ser Leu Arg His Asn
                85                  90                  95

Asn Leu Ser Phe Ile Thr Pro Gly Ala Phe Lys Gly Leu Pro Arg Leu
            100                 105                 110

Ala Glu Leu Arg Leu Ala His Asn Gly Asp Leu Arg Tyr Leu His Ala
        115                 120                 125

Arg Thr Phe Ala Ala Leu Ser Arg Leu Arg Arg Leu Asp Leu Ala Ala
    130                 135                 140

Cys Arg Leu Phe Ser Val Pro Glu Arg Leu Leu Ala Glu Leu Pro Ala
145                 150                 155                 160

Leu Arg Glu Leu Ala Ala Phe Asp Asn Leu Phe Arg Arg Val Pro Gly
                165                 170                 175

Ala Leu Arg Gly Leu Ala Asn Leu Thr His Ala His Leu Glu Arg Gly
            180                 185                 190

Arg Ile Glu Ala Val Ala Ser Ser Leu Gln Gly Leu Arg Arg Leu
        195                 200                 205

Arg Ser Leu Ser Leu Gln Ala Asn Arg Val Arg Ala Val His Ala Gly
    210                 215                 220

Ala Phe Gly Asp Cys Gly Val Leu Glu His Leu Leu Leu Asn Asp Asn
225                 230                 235                 240

Leu Leu Ala Glu Leu Pro Ala Asp Ala Phe Arg Gly Leu Arg Arg Leu
                245                 250                 255

Arg Thr Leu Asn Leu Gly Gly Asn Ala Leu Asp Arg Val Ala Arg Ala
            260                 265                 270

Trp Phe Ala Asp Leu Ala Glu Leu Glu Leu Tyr Leu Asp Arg Asn
        275                 280                 285

Ser Ile Ala Phe Val Glu Glu Gly Ala Phe Gln Asn Leu Ser Gly Leu
    290                 295                 300

Leu Ala Leu His Leu Asn Gly Asn Arg Leu Thr Val Leu Ala Trp Val
```

-continued

```
            305                 310                 315                 320
Ala Phe Gln Pro Gly Phe Phe Leu Gly Arg Leu Phe Leu Phe Arg Asn
                    325                 330                 335

Pro Trp Cys Cys Asp Cys Arg Leu Glu Trp Leu Arg Asp Trp Met Glu
                340                 345                 350

Gly Ser Gly Arg Val Thr Asp Val Pro Cys Ala Ser Pro Gly Ser Val
            355                 360                 365

Ala Gly Leu Asp Leu Ser Gln Val Thr Phe Gly Arg Ser Ser Asp Gly
        370                 375                 380

Leu Cys Val Asp Pro Glu Glu Leu Asn Leu Thr Thr Ser Ser Pro Gly
385                 390                 395                 400

Pro Ser Pro Glu Pro Ala Ala Thr Thr Val Ser Arg Phe Ser Ser Leu
                405                 410                 415

Leu Ser Lys Leu Leu Ala Pro Arg Val Pro Val Glu Glu Ala Ala Asn
            420                 425                 430

Thr Thr Gly Gly Leu Ala Asn Ala Ser Leu Ser Asp Ser Leu Ser Ser
        435                 440                 445

Arg Gly Val Gly Gly Ala Gly Arg Gln Pro Trp Phe Leu Leu Ala Ser
    450                 455                 460

Cys Leu Leu Pro Ser Val Ala Gln His Val Val Phe Gly Leu Gln Met
465                 470                 475                 480

Asp
```

```
<210> SEQ ID NO 3
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(20)
<223> OTHER INFORMATION: forward primer for polymorphism 506B13CA1
      (DXS10042)

<400> SEQUENCE: 3
atcacagtgc cctgcctaaa                                                    20

<210> SEQ ID NO 4
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(20)
<223> OTHER INFORMATION: reverse primer for polymorphism 506B13CA
      (DXS10042)

<400> SEQUENCE: 4
tcccaaagtg ctgggattac                                                    20

<210> SEQ ID NO 5
<211> LENGTH: 21
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(21)
<223> OTHER INFORMATION: forward primer for polymorphism 200L4CA1
      (DXS10044)

<400> SEQUENCE: 5
```
gaacagcaaa ccaaatccaa a                   21

<210> SEQ ID NO 6
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(20)
<223> OTHER INFORMATION: reverse primer for polymorphism 200L4CA1
      (DXS10044)

<400> SEQUENCE: 6
ggcctatggt aatgcctcct                    20

<210> SEQ ID NO 7
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(20)
<223> OTHER INFORMATION: forward primer for polymorphism 169I5CA2
      (DXS10045)

<400> SEQUENCE: 7
aaacttagct gggcatgctg                    20

<210> SEQ ID NO 8
<211> LENGTH: 21
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(21)
<223> OTHER INFORMATION: reverse primer for polymorphism 169I5CA2
      (DXS10045)

<400> SEQUENCE: 8
gctgggacta catacagcac a                   21

<210> SEQ ID NO 9
<211> LENGTH: 21
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(21)
<223> OTHER INFORMATION: forward primer for NYX expression

<400> SEQUENCE: 9
agggagtgga ggggacctca g                   21

<210> SEQ ID NO 10
<211> LENGTH: 18
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(18)
<223> OTHER INFORMATION: reverse primer for NYX expression

<400> SEQUENCE: 10

```
                                                     -continued
acggcacgga cgcggttg                                                          18

<210> SEQ ID NO 11
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(20)
<223> OTHER INFORMATION: forward primer for W350X mutation

<400> SEQUENCE: 11
gatttttcct ggggtgacct                                                        20

<210> SEQ ID NO 12
<211> LENGTH: 19
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(19)
<223> OTHER INFORMATION: reverse primer for W350X mutation

<400> SEQUENCE: 12
gtccaggtcg atggagacc                                                         19

<210> SEQ ID NO 13
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(20)
<223> OTHER INFORMATION: forward primer for segregation analysis of
      deletion mutation

<400> SEQUENCE: 13
gatttttcct ggggtgacct                                                        20

<210> SEQ ID NO 14
<211> LENGTH: 19
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(19)
<223> OTHER INFORMATION: reverse primer for segregation analysis of
      deletion mutation

<400> SEQUENCE: 14
gtccaggtcg atggagacc                                                         19
```

GPI-ANCHORED SMALL LEUCINE-RICH PROTEOGLYCAN GENE NYX

FIELD OF THE INVENTION

The present invention is related to a gene encoding a novel small leucine-rich proteoglycan gene. In particular, this invention relates to a mammalian gene herein referred to as NYX, encoding a proteoglycan referred to as nyctalopin, wherein mutations of NYX may cause complete X-linked congenital stationary night blindness.

BACKGROUND

During mammalian retinal development a complex sequence of molecular events leads to the precise laminations and interconnections of the mature retina. In normal mature human retinas, rod and cone photoreceptors start the processing of vision, which proceeds through bipolar and ganglion cell retinal pathways to the brain [1]. Hereditary disease can perturb these retinal pathways and cause either progressive degeneration or more stationary visual deficits [2]. Congenital stationary night blindness (CSNB) is a group of retinopathies that fall into the latter category of a selective retinal pathway disturbance that manifest at birth. CSNB has been recognized clinically for more than 100 years; genetic subtypes have been defined; and different sites of disease action have been postulated [3–5].

Patients with X-linked CSNB phenotypically exhibit normal fundi, but generally have reduced visual acuity, impaired night vision and, in addition, may exhibit myopia (or occasionally hyperopia), and nystagmus. Based on electroretinographic findings, patients with X-linked CSNB can have one of two forms of X-linked CSNB—complete or incomplete [4,6]. This clinical heterogeneity correlates with underlying genetic heterogeneity in which complete X-linked CSNB segregates with the CSNB1 locus in Xp11.4, and incomplete X-linked CSNB segregates with the CSNB2 locus in Xp11.23 [6,7]. Patients with incomplete X-linked CSNB who show both impaired rod and cone function were recently shown to have mutations in a voltage-gated L-type calcium channel $\alpha\text{-}1_F$-subunit gene, CACNA1F [8,9]. The electroretinographic findings in patients with complete X-linked CSNB indicates a specific defect in the ON pathway of the retina, namely the retinal circuitry which transmits the visual signal from the majority if not all of the rod photoreceptor cells and a subset of the cone photoreceptors. This signal is mediated via the rod and cone on-bipolar retinal neurons.

The biochemical defects underlying complete X-linked CSNB is unknown but may be revealed by identifying the gene, CSNB1, involved in this disorder. The CSNB1 locus was reported to be on the proximal portion of the human X chromosome, between DXS556 and DXS8083, as described previously [6].

The identification of the gene which is causative of complete X-linked CSNB may allow for development of diagnostic tests for this disorder and risk assessment in members of affected families. As well, identification of the gene that is causative of complete X-linked CSNB will provide information as to the basic defect in this retinal condition, which could lead to effective methods for treatment or cure of the disorder. In as much as the identification of the gene for complete X-linked CSNB and its encoded protein will provide understanding of the general mechanism of neurotransmission and the development of neuronal circuitry [1], this discovery may have implications for understanding the formation of neural circuits in general.

Leucine-rich repeat glycoproteins form part of the extracellular matrix (ECM) of mammalian cells [10]. The major components of the ECM are collagens, proteoglycans, glycosaminoglycans, fibronectin and, to a lesser extent, glycoproteins. These components are organized into a fibrillar meshwork, to provide mechanical strength and elasticity, and to create a structural framework that provides a substratum for cell adhesion and migration. The ECM plays an integral role in the pivotal processes of development, tissue repair, and metastasis. Within the ECM, the leucine-rich repeat glycoproteins are likely to perform more than a structural role, and also likely to be involved in regulating cell growth, adhesion and migration.

Many cell-surface proteins are anchored to the external surface of the plasma membrane by covalently attached glycosyl-inositol phospholipids ("GPIs"). These anchors use a common structure as a general mechanism for membrane attachment, irrespective of protein function, and are added post-translationally at the time of the translocation of the protein across the endoplasmic reticulum [11].

The N-terminus of a secreted protein usually consists of a cleavable leader of 15–30 amino acids, which is called a signal sequence. The signal sequence is both necessary and sufficient for transfer of any attached polypeptide to the target membrane and is responsible for directing ribosomes to attach to the endoplasmic reticulum as soon as the first few N-terminal amino acids are synthesized [12].

The identification of the gene, mutations of which cause complete X-linked CSNB, will aid in the elucidation of the role of the protein in retinal function, and neurotransmission. Knowledge of the structure of this gene, from both naturally occurring mutations and engineered variants of the protein, will lead to studies of the structure-function relationships of the protein in the cellular environment and its role in the disease process. Further, the identification of the gene will provide a tool for the diagnosis of complete X-linked CSNB in individuals suspected of having this disorder.

SUMMARY OF THE INVENTION

The complete sequence of a gene on the short arm of the X-chromosome, herein referred to as NYX, has been elucidated. NYX has homology to members of the Small Leucine-Rich Proteoglycan (SLRP) family of genes, which is a subfamily of the leucine-rich repeat superfamily of proteins. Moreover, the NYX-encoded protein is GPI-anchored and is the only leucine-rich repeat protein known to the Applicant that is GPI-anchored. Mutational analysis of NYX in 22 families with complete X-linked CSNB has identified 14 different mutations that are predicted to cause missense, insertion, stop, or deletion mutations in the protein product of NYX, herein referred to as nyctalopin. Together, these findings establish that mutations in NYX cause complete X-linked CSNB.

The present invention provides a mammalian nucleotide sequence encoding a novel small leucine-rich proteoglycan strongly expressed in the retina and also in the kidney. Thus, in one aspect, this invention is an isolated, recombinant or synthetic DNA molecule comprising a sequence of nucleotides that encodes a mammalian GPI-anchored small leucine-rich proteoglycan which is expressed in tissues including the kidney and the retina.

In one embodiment, the invention comprises an isolated, recombinant or synthetic DNA molecule having a sequence of nucleotides selected from a group comprising of sequences which encode for nyctalopin; an amino acid sequence which is at least 50% homologous to nyctalopin;

the amino acid sequence of SEQ ID NO: 2; or an amino acid sequence which is at least 50% homologous to SEQ ID NO: 2. In another embodiment, the invention comprises an isolated, recombinant or synthetic DNA molecule or polynucleotide comprising a nucleotide sequence which is: SEQ ID NO: 1; substantially homologous to SEQ ID NO: 1; or a sequence that hybridizes under stringent conditions to a hybridization probe having a nucleotide sequence of SEQ ID NO: 1 or the complement of SEQ ID NO: 1. The polynucleotide may be selected from the group comprising:

(a) RNA;

(b) cDNA;

(c) genomic DNA; and (d) synthetic nucleic acids.

In another aspect, this invention comprises a substantially pure mammalian GPI-anchored small leucine-rich proteoglycan, represented by the sequence of amino acids set forth in FIG. 7 (SEQ ID NO:2); SEQ ID NO:2 having at least one conservative amino acid substitution; or an amino acid sequence which is at least 50% homologous to SEQ ID NO:2.

In another embodiment, the invention comprises a protein molecule that encodes a murine GPI-anchored small leucine-rich proteoglycan, which is the homologue of the human GPI-anchored human small leucine-rich proteoglycan.

In another aspect, this invention comprises an isolated RNA sequence that encodes a mammalian GPI-anchored small leucine-rich proteoglycan, including a human or murine GPI-anchored small leucine-rich proteoglycan. This invention also comprises an antisense RNA molecule having a sequence that is complementary to the mRNA encoding a mammalian GPI-anchored small leucine-rich proteoglycan, including a human or murine GPI-anchored small leucine-rich proteoglycan.

In another aspect, this invention comprises an expression vector, preferably a mammalian expression vector, comprising the nucleotide sequence of a mammalian GPI-anchored small leucine-rich proteoglycan which may be expressed in tissues including the kidney and the retina.

In another aspect, the invention comprises a method and diagnostic kit of diagnosing complete X-linked CSNB, which method and kit includes the step of and means for screening for alterations in the sequence of nucleotides disclosed herein.

In another aspect, the invention may include a method of screening molecules which affects expression or production of nyctalopin wherein said method comprises the step of exposing primary or NYX transfected cells to a drug candidate and determining the level of transcription or translation of NYX gene products.

BRIEF DESCRIPTION OF THE FIGURES

FIG. 1: Phenotype of complete X-linked CSNB. FIG. 1A: The electroretinogram of a patient compared with an age-matched normal. FIG. 1B: Rod and L/M cone sensitivities measured on a 12 degree grid across the visual field of a patient. FIG. 1C: Spectral sensitivity measurements, dark-adapted, in a representative normal subject (open squares) and the patient (filled triangles).

FIG. 3B: The amino acid sequence (SEQ ID NO.: 2) of nyctalopin shows homology with members of the SLRP family of proteins. The protein has 11 leucine-rich repeat motifs with a 24 amino acid consensus for small leucine-rich proteoglycans with cysteine clusters flanking the repeat core of the protein. The conserved amino acids are shown in bold.

FIG. 4: cDNA expression profile of NYX in various human tissues. FIG. 4A: Upper panel shows a 755 bp fragment of the NYX mRNA in retina and kidney tissue samples. Lower panel shows the 281 bp fragment of EST JRL4A1 which serves as a positive control. FIG. 4B: Using a NYX-antisense digoxigenin-labelled riboprobe (NYX-AS) for in situ hybridization in human retinal sections showing the expression of NYX in the inner segment (IS) of photoreceptors, in the outer- and inner-nuclear layers (ONL, INL), and in the ganglion cell layer (GCL). FIG. 4C: No significant staining was observed using a NYX-sense probe. FIG. 4D: Rhodopsin-antisense probe (RHO-AS) labelled rod photoreceptors in the IS and ONL.

FIG. 5A: Identification of a putative nonsense mutation in families 610 and 620 in exon 3 (at nucleotide 1049) caused by a G to A transition, which changes a Trp to a stop codon. Segregation analysis of this mutation was performed by restriction endonuclease digestion. Affected individuals show the loss of a FokI restriction site, female carriers have fragments indicating both the presence and absence of this restriction site, and unaffected males show only the FokI site. FIG. 5B: Identification of a 24-bp deletion observed in seven (six shown) different families. This mutation results in the loss of eight amino acids beginning at codon 29. The segregation of the 24-bp deletion was performed by PCR amplification of genomic DNA and the products were subjected to agarose gel electrophoresis. The presence of the smaller PCR fragment representing the deletion was observed in affected males and carrier females. FIG. 5C: Identification of an insertion mutation of 21 nt between nucleotides 444 and 445 in patient 650-1, which results in the addition of seven amino acids to the protein. FIG. 5D: Identification of a missense mutation in patient P520-IV-27 caused by a T to A transversion at nucleotide 638, which changes a Leu codon to a Gln codon.

FIG. 6: Summary of the 14 mutations of NYX detected in 22 families with complete X-linked CSNB. Mutation refers to the position of the nucleotide changes, including insertions, deletions and changes. 'Codon change' shows the codons which have been changed by the mutations in NYX.

FIG. 7: Nucleotide sequence of human NYX (SEQ ID NO:1) with the amino acid sequence of nyctalopin in single letter code underneath (SEQ ID NO:2).

DETAILED DESCRIPTION OF THE INVENTION

Figure 2:
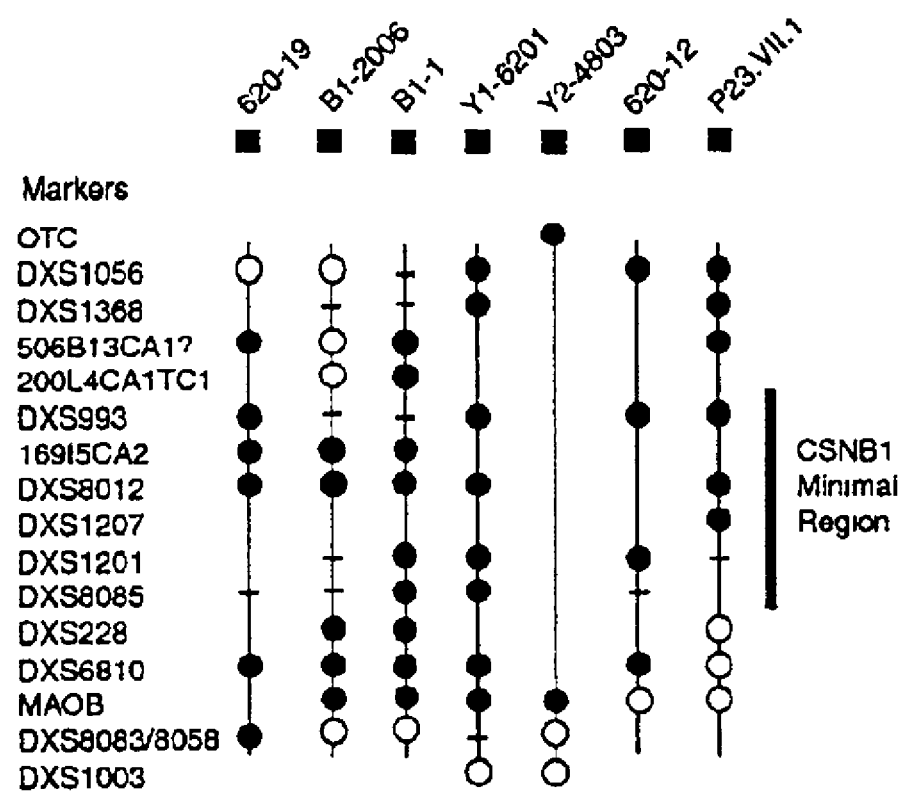
FIG. 2: Genetic characterization and physical map of the minimal region for the CSNB1 locus. (a) Families with X-linked complete CSNB were analyzed with genetic markers from the Xp11 region to define the boundaries of the chromosomal position of the CSNB1 locus. The chromosomal region from seven males that were analysed is indicated by the seven vertical lines. The thin black vertical line on the right indicates the minimal genetic region established for the CSNB1 gene.

The details of the preferred embodiments of the present invention are set forth in the accompanying drawings and description below. Based on the details of the invention described herein, numerous additional innovations and changes will become obvious to one skilled in the art.

Unless otherwise indicated, all terms used herein have the same meaning as is commonly understood by one skilled in the art of the present invention. Practitioners are particularly directed to *Current Protocols in Molecular Biology* (Ausubel) or Maniatis et al., Cold Spring Harbor, N.Y., Cold Spring Harbor Laboratory (1990), for terms of the art.

The term "carrier" refers to a female who is heterozygous for a single recessive gene and does not have the phenotype associated with complete X-linked CSNB. The terms "isolated" or "substantially pure" nucleic acid or polynucleotide (e.g., an RNA, DNA or a mixed polymer) is one that is substantially separated from other cellular components that naturally accompany a native human sequence or protein, e.g., ribosomes, polymerases, many other human genome sequences and proteins. The term embraces a nucleic acid sequence that has been removed from its naturally occurring environment, and includes recombinant or cloned DNA isolates and chemically synthesized analogs or analogs that are biologically synthesized by heterologous systems.

The term "encode" refers to the following: DNA or a polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

The term "expression vector" refers to a recombinant DNA construct that comprises, among other elements, a DNA sequence of which expression is desired. An "expression vector" is used to introduce heterologous DNA into cells for expression of the heterologous DNA, as either an episomal element, or after incorporation into the cellular genome. An "expression vector" will contain all of the elements necessary for transcription of the DNA sequence functionally linked to the DNA sequence, including but not limited to a transcription initiation element, a transcription termination element, and elements that modulate expression of the DNA sequence, such as promoters or enhancers. These elements may be native to the DNA sequence of which expression is desired. An expression vector may contain elements that will regulate translation, if translation of the resultant RNA transcript into a protein product is desired.

The term "heterologous" refers to DNA or RNA that does not occur, in nature, as part of the genome in which it is present, which is found in a location or locations in the genome that differ from that in which it occurs in nature, or which is present in the genome as a result of human manipulation of the genome. It is DNA or RNA that is not endogenous to the cell in which it is found, or that is endogenous to the cell but which has been manipulated in vitro, and has been artificially introduced into the cell. Heterologous DNA or RNA need not be incorporated into the host cell genome, but may be maintained episomally.

The term "nyctalopin" refers to the protein encoded by NYX, and includes variants thereof which occur in nature or which can be generated experimentally. Such variants include proteins that have conservative amino acid substitutions, or those which have alterations in amino acid sequence that affect protein function. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native nyctalopin sequence, preferably in excess of about 90%, and more preferably at least about 95% homologous. Also included are proteins encoded by DNA which hybridize under high or low stringency conditions, to nyctalopin-encoding nucleic acids and closely related polypeptides or proteins retrieved by antisera to nyctalopin.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity. Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

The terms "isolated", "substantially pure", "purified", "purified and isolated" and "substantially homogeneous" are used interchangeably to describe a protein or polypeptide that has been separated from components that accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "NYX" refers to the gene that encodes for nyctalopin, and includes untranslated regions and regulatory and promoter sequences which influence the expression of the gene and the translation of the transcript. In the appropriate context, NYX may refer to the cDNA product of this gene or other polynucleotides. These nucleic acids comprise a sequence which is either derived from, or substantially similar to a natural nyctalopin-encoding gene or one having substantial homology with a natural nyctalopin-encoding gene or a portion thereof.

The term "substantial homology or similarity" when referring to a nucleic acid or fragment thereof indicates that when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or similarity exists when a nucleic acid or fragment thereof hybridizes to another nucleic acid (or a complementary strand thereof)

under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30.degree. C., typically in excess of 37.degree. C., and preferably in excess of 45.degree. C. Stringent salt conditions will ordinarily be less than 1000 mM, typically less than 500 mM, and preferably less than 200 mM. However, the combination of parameters is much more important than the measure of any single parameter. See, e.g., Wetmur and Davidson, 1968. Probe sequences may also hybridize specifically to duplex DNA under certain conditions to form triplex or other higher order DNA complexes. The preparation of such probes and suitable hybridization conditions are well known in the art. Generally, the terms "high stringency" or "conditions of high stringency" generally means washing at low salt concentration, less than about 0.2 and preferably about 0.1 SSPE, and at high temperature, more than about 60° C. and preferably about 65° C. It will be understood that an equivalent stringency may be achieved by using alternative buffers, salts and temperatures.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "precursor" refers to a protein with the amino acid sequence corresponding to the sequence of the full length MRNA which, upon translation, results in a protein which may be further processed to form the mature nyctalopin.

The term "antibodies" refers to polyclonal and/or monoclonal antibodies and fragments thereof, and immunologic binding equivalents thereof, which are capable of specifically binding to the nyctalopin and fragments thereof or to polynucleotide sequences from the NYX locus or a portion thereof. The term "antibodies" is used both to refer to a homogeneous molecular entity, or a mixture such as a serum product made up of a plurality of different molecular entities. Polypeptides may be prepared synthetically in a peptide synthesizer or as fusion proteins as described above and coupled to a carrier molecule (e.g., keyhole limpet hemocyanin) and injected over several months into rabbits, mice, goats, etc. Sera is tested for immunoreactivity to nyctalopin or fragment. Monoclonal antibodies may be made by injecting mice with the protein polypeptides, fusion proteins or fragments thereof. Monoclonal antibodies are screened by ELISA and tested for specific immunoreactivity with nyctalopin or fragments thereof. These antibodies will be useful in assays and as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typically the injections are performed in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of 10.sup.-8 M.sup.-1 or preferably 10.sup.-9 to 10.sup.-10 M.sup.-1 or stronger are typically made by standard procedures as described, e.g., in Harlow and Lane, 1988 or Goding, 1986. Briefly, appropriate animals are selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437;

4,275,149 and 4,366,241. Also, recombinant immunoglobulins may be produced (see U.S. Pat. No. 4,816,567).

The term "epitope" refers to a region of a polypeptide that provokes a response by an antibody. This region needs not comprise consecutive amino acids. The term epitope is also known in the art as "antigenic determinant".

Mapping the Location of the Gene for Complete X-linked CSNB

The CSNB1 locus was previously reported to be located on the proximal portion of the human X chromosome, between DXS556 and DXS8083 [6]. By analyzing additional families with complete X-linked CSNB, and by using new polymorphic markers developed on the basis of dinucleotide repeats within this minimal region, the minimal region can be further refined. Analysis of selected recombinant X chromosomes in the set of families with complete X-linked CSNB moves the distal boundary of the CSNB1 minimal region from DXS556 to the interval between 200L4CA1 and DXS8012 (FIG. 2 and FIG. 3($a$)). From further analysis, the proximal crossover previously observed in patient V:1 in family P23 [19] limits the proximal boundary to between DXS1207 and DXS228 (FIG. 2 and FIG. 3($a$)). Therefore, the minimal region for the CSNB1 locus is limited to the interval between 200L4CA1 and DXS228 in Xp11.4. The methods used for localizing genes on human chromosomes using these and other techniques are known to those skilled in the art.

Identification of a Candidate Gene for CSNB1

To position genetic markers accurately across the CSNB1 minimal region and identify candidate genes for the CSNB1 locus, a robust physical map of the CSNB1 minimal region in Xp11.4 may be developed. A subset of BAC and PAC clones from the minimal tiling path of the estimated 1.2 Mb CSNB1 minimal region is sequenced to between 1–2.7-fold redundancy. A sub-library is constructed [20] for each of the BAG clones and random clones from each sub-library are sequenced with the aid of ABI 373 or ABI 377 sequencing machines and fluorescently labeled primers (ABI, Amersham). DNAStar™ software is used for gel trace analysis and contig assembly as well as DNA and protein alignments. DNA and protein sequences are then examined against available public databases using the various Blast™ programs available through the network server at the National Center for Biotechnology Information. A novel open reading frame is present in this region, which the Applicant has designated to be the NYX gene.

Candidates for the CSNB1 gene are expected to be expressed in the retina and located in the CSNB1 minimal region. Expression of NYX is assessed by PCR amplification of a QUICK-Screen™ Human cDNA Library Panel (Clontech), using primers which span exons 1 to 3. PCR products are electrophoresed through a 1% agarose gel and visualized by ethidium bromide staining. The 755-bp PCR product is detected robustly in the retinal and kidney cDNA library (FIG. 3). RNA in situ hybridization is performed as described [21–23], using a 668-bp antisense probe (from nt1557-2224 of the cDNA). These studies reveal that retinal expression of NYX occurs predominantly in the inner- and outer-nuclear layers of the human retina but is also seen in some cells of the ganglion cell layer (FIG. 4).

The extended NYX cDNA sequence is established by sequencing of PCR and RACE products using first-strand cDNA from total human retinal RNA as the template for PCR. Touchdown PCR using the Failsafe™ PCR Premix Selection Kit is carried out according to the manufacturer's protocol (Epicentre Technologies). RACE is carried out using Human Retina cDNA Marathon-Ready™ cDNA (Clontech). A secondary amplification using a nested NYX primer is performed. RACE and PCR products are gel purified using the Concert™ Gel Extraction kit (Life Technologies) and sequenced using the ThermoSequenase™ P-radiolabelled terminator cycle sequencing kit (Amersham Life Science). To establish the genomic organization of the NIX gene, the full-length cDNA sequence of NYX is compared to the genomic sequence derived from our analysis of BAC clone 378P5 and that produced by the Sanger Centre for BAC clone 16915.

Figure 7:
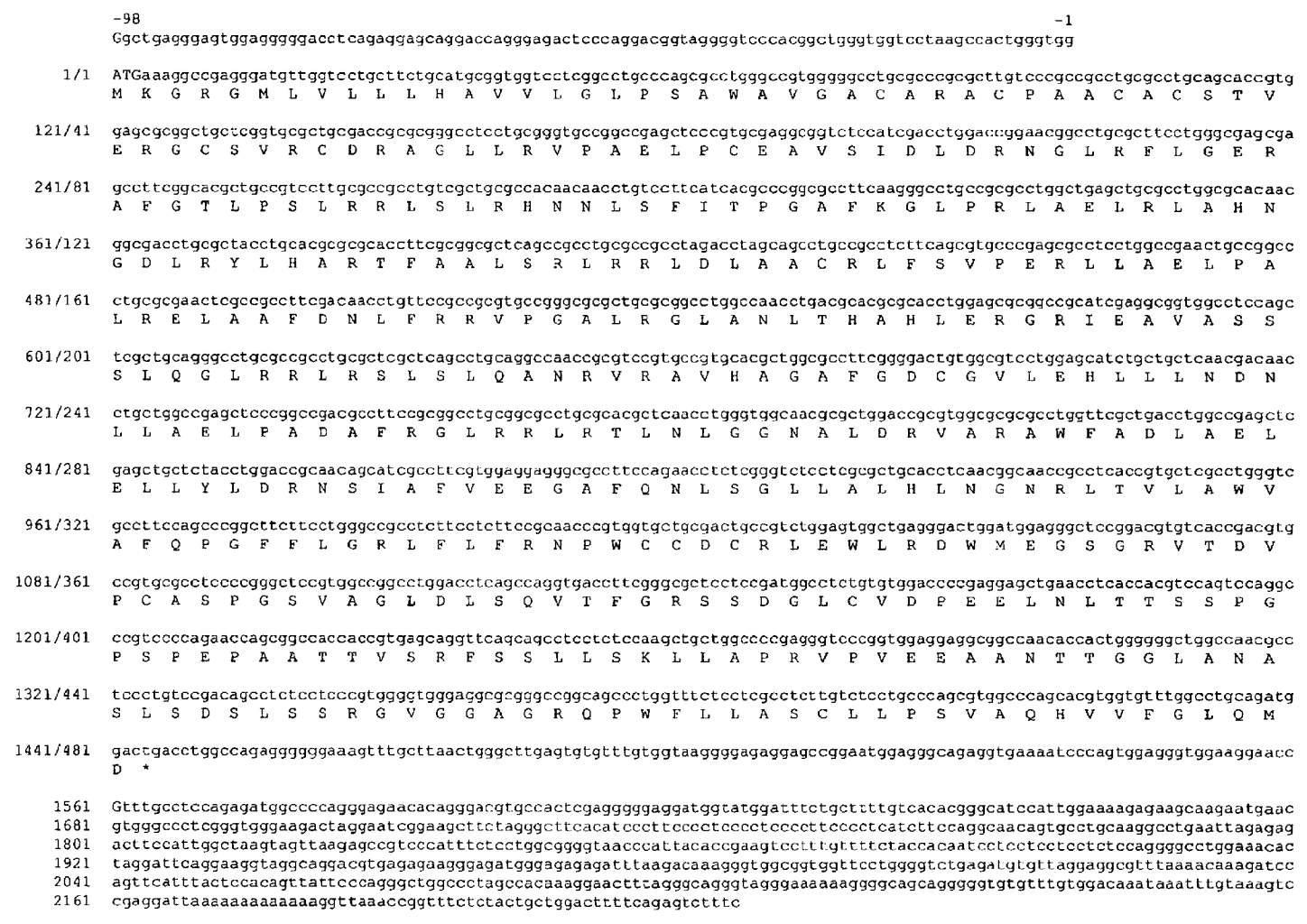

The cDNA sequence of NYX consists of a 1443 bp open reading frame that codes for a protein of 481 amino acids (FIG. 7). The 5'-untranslated region is 98 bp long, and the translation initiation site lies in exon 2. A polyadenylation site lies 688 nt downstream from the stop codon of the open reading frame, and the 3'-untranslated region is at least 753 bp long. On the X chromosome, NYX is organized in three exons, spanning 28 kb of genomic sequence. The 3'-end lies 26 kb distal to the proximal end of PAC clone 16915 (FIG. 3). The open reading frame of NYX is contained in exons 2 and 3. Intron 2 spans 25.5 kb and encompasses the marker DXS8012.

Characteristics of Nyctalopin

NYX encodes a 481 ammo acid protein, herein called nyctalopin, which has sequence similarity with members of the superfamily of proteins containing tandem arrays of the leucine-rich repeat (LRR) motif [10,13]. Such proteins are known to function in protein—protein interactions, especially in matrix assembly, and therefore nytalopin may possibly be mediating specific neural connections between cells in the retina. Moreover, the presence of the 24 amino acid consensus: x-x-I/V/L-x-x-x-x-F/P/L-x-x-L/P-x-x-L-x-x-L/I-x-L-x-x-N-x-I/L (where I,V,L,F,P and N are single letter amino acid codes and "x" represents any amino acid) in the core protein with cysteine clusters flanking the LRR domain (see FIG. 3B) [SEQ ID NO: 2], qualifies nyctalopin as a new member of the subfamily of small leucine-rich proteoglycans (SLRPs) [10]. From a homology comparison of nyctalopin with other SLRP proteins, it is evident that nyctalopin is a unique member of this subfamily and the LRR superfamily in general. Nyctalopin has five putative consensus sequences (N-X-(S/T)) necessary for substitution by N-linked oligosaccharides or keratan sulfate [14], three of these sequences lie within the LRR region. The $NH_2$-terminal end of nyctalopin is predicted [15] to contain a membrane signal peptide with a putative cleavage site between amino acid 23 and 24. AWA-VG (FIG. 3). In addition, the carboxyl-terminal region of nyctalopin contains a GPI-anchor signal sequence, including the requisite GPI N-terminal signal sequence (amino acids 339 to 379), the C-terminal hydrophobic region (last 22 amino acids) and a potential cleavage site at amino acids 445–447 [16] (FIG. 3B) [SEQ ID NO: 2. The identification of these sites was accomplished at the website www.expasy.expasy.ch/tools and is well known to those skilled in the art. Thus, NYX codes for a GPI-anchored proteoglycan with a putative membrane signal peptide. Without being limited to a theory, these results suggest that the clinical features of complete X-linked CSNB can be explained by the presence of a mutant nyctalopin (or entire absence of nyctalopin) causing the disruption of selected connections or interactions between retinal neurons, including those of the retinal ON-bipolar pathway, possibly during early stages of embryonic development.

It is understood that, because of genetic redundancy, the nucleotide sequence of NYX disclosed herein may be modified by making variations in sequence that do not alter the amino acid sequence of the resultant protein. The nucleotide sequence may also be modified to make conservative amino acid substitutions to the resultant protein, which do not alter, or do not significantly alter, the biological activity of the resulting molecule. The resulting modified nucleotide sequences are contemplated herein.

It is understood that the amino acid sequence of nyctalopin disclosed herein may be modified by making minor variations in sequence, such as conservative amino acid substitutions or minor deletions or insertions that do not alter the activity of the protein, and the resulting modified proteins are contemplated herein. Suitable conservative substitutions of amino acids are known to those of skill in this art, and may be made generally without altering, or significantly altering, the biological activity of the resulting molecule. Such substitutions may also be made empirically.

Expression Systems

For expression of NYX or nyctalopin, eukaryotic or prokaryotic expression systems may be designated in which the NYX sequence is introduced into a plasmid or other vector which is then introduced into living cells. Expression vectors may contain the entire open reading frame of NYX or alternatively, only portions of the normal, polymorphic or mutant NYX sequences.

Typical expression vectors contain promoters that direct the synthesis of large amounts of mRNA corresponding to the sequence to be expressed. They may also contain, among other things, sequences that allow for autonomous replication within the host organism, sequences that encode positive or negative selectable markers, and sequences that increase the efficiency of mRNA translation. Expression vectors may be maintained in a cell as freely replicating entities by using regulatory elements of viruses, or alternatively cell lines may be produced which have integrated the expression vector or a part thereof into the genomic DNA.

Expression of foreign sequences in bacteria such as *E. coli* requires the insertion of the sequence into a vector, usually a plasmid, which contains several elements such as sequences encoding a selectable marker genes, a controllable transcription promoter, translation control sequences and a polylinker. A relatively simple vector that can be used in *E. coli* is pBluescript™ which utilizes the lacZ promoter and a neighbouring lacZ gene whose function is disrupted when the foreign gene sequence is inserted into the vector.

In vitro expression of vectors which use the T7 late-promoter expression system or plasmid vectors containing late promoters and the corresponding RNA polymerases from related bacteriophages such as T3, T5 and SP6 may be used for in vitro production of proteins from cloned DNA. E. coli can also be used for expression by infection with M13 Phage mGPI-2.

Eukaryotic expression systems can be used if appropriate post-translational modification of expressed proteins is desired. This allows for studies of the NYX gene and gene product including, for example, determination of the post-translational modifications required for biological activity or identifying regulatory elements in the 5' region of the gene and their role in tissue regulation of protein expression. Expression in eukaryotic systems will permit the production of large amounts of normal functional protein and mutant protein for isolation and purification, and provides cells which express NYX and can be used as a functional assay system, such as for testing of the effectiveness of pharmacological agents or studying the function of the normal protein, naturally occurring polymorphisms, artificially produced mutated proteins, or specific portions thereof.

In order to produce mutated or polymorphic proteins, the NYX sequence can be altered using procedures such as DNA polymerase fill-in, exonuclease deletion, terminal deoxynucleotide transferase extension, ligation of synthetic DNA sequences and site-directed sequence alteration using specific oligonucleotides generated by PCR.

Once an expression vector containing NYX or a portion thereof is constructed, it is introduced into an appropriate E. coli strain by transformation techniques including calcium phosphate transfection, DEAE-dextran transfection, electroporation, microinjection, protoplast fusion and liposome-mediated transfection. The host to be transfected with the expression vector of this invention may be selected from the group consisting of E.coli, Pseudomonas, Bacillus subtilis, or other bacilli or bacteria, yeast, fungi, insect (using baculoviral vectors for expression), mouse or other animal or human tissue cells. Mammalian cells can also be used to express the nyctalopin using a vaccinia virus expression system.

Prokaryotic and eukaryotic expression systems allow various important functional domains of the protein to be recovered as fusion proteins and used for binding, structural and functional studies and also for the generation of appropriate antibodies.

Fusion proteins are particularly advantageous because they provide a system for ensuring high levels of expression of the protein of interest and relatively simple purification thereof. In order to make a nyctalopin fusion protein, the NYX sequence is inserted into a vector which contains a nucleotide sequence encoding the amino terminus of a protein that is abundantly expressed (eg. GST—glutathionine succinyl transferase). The NYX sequence is inserted 3' and in frame to this nucleotide sequence, is expressed and recovered from the prokaryotic (eg. bacterial or baculovirus) or eukaryotic cells. The fusion protein can then be purified by affinity chromatography and, if desired, the nyctalopin obtained by enzymatic cleavage of the fusion protein.

The preparation of substantially purified nyctalopin or fragments thereof allows the determination of the protein tertiary structure by x-ray crystallography or by NMR. Determination of structure may aid in the design of pharmaceuticals to interact with the protein, alter protein charge configuration or charge interaction with other proteins, or to alter its function in the cell.

Mutation and Segregation Analysis of NYX

To identify which mutations in NYX cause complete X-linked CSNB, primers flanking and internal to each exon are used for direct DNA sequence analysis of the entire NYX gene in affected individuals from families with complete X-linked CSNB. Primers are designed, genomic DNA is amplified and PCR products are purified and sequenced using methods known to those skilled in the art.

Once a DNA sequence change is identified by the mutation analysis, aside from DNA sequencing, segregation analysis may be accomplished by a number of techniques. Allele sizing, as described in [18] can be used to follow as little as a single base-pair insertion or deletion in a gene. Alternatively, the segregation of a larger insertion or deletion, such as the 24 bp deletion mutation found in one patient with complete X-linked CSNB, can be followed by PCR analysis and gel electrophoresis. Primers are used to amplify by PCR, in affected, non-affected and carrier individuals, the region that encompasses the deletion (or insertion) of the nucleotide sequence. After electrophoresis of the amplified products on an agarose gel (or a polyacrylamide gel), the deletion (or insertion) is detected by the presence of a PCR fragment which is smaller (or larger) than the PCR fragment from a normal gene.

Alternatively, segregation analysis may be accomplished by following the loss or gain of restriction endonuclease recognition sites (restriction sites). Mutated and wild-type sequences are analyzed by a DNA analysis program, for example DNA Strider1.2™, looking for changes in DNA sequence that would result in a loss or gain of a restriction site. Once found, these changes can be used to track the mutation in families of affected individuals. Firstly, PCR is used to amplify the region of interest from the genomic DNA of affected, non-affected and carrier individuals. The PCR products are digested with the enzyme that will detect the mutation (in either a positive or negative sense). The digested products are electrophoresed through agarose and visualized to determine whether the restriction enzyme site is present or not, whichever the case may be, in the individual analysed.

Numerous additional methods for identifying mutations of NYX in individuals, or tracing mutations of NYX through families are obvious to one skilled in the art. Other useful diagnostic techniques include, but are not limited to:

(a) direct DNA sequencing;

(b) analysis of restriction length polymorphism;

(c) single-stranded conformation analysis or heteroduplex analysis;

(d) RNAse protection;

(e) the use of proteins that recognize nucleotide mismatches, such as the E. coli mutS protein;

(f) single nucleotide extension assays;

(g) microchip technology analysis;

(h) Northern blot analysis;

(i) Southern blot analysis;

(j) dot blot analysis;

(k) PCR analysis;

(l) fluorescent in situ hybridization analysis; and (m) two-step label amplification analysis;

(n) PFGE analysis; and (o) allele-specific oligonucleotide (ASO) analysis.

The newly developed technique of nucleic acid analysis via microchip technology is also applicable to the present invention. In this technique, thousands of distinct oligonucleotide probes are embedded in an array on a silicon or glass chip. Nucleic acid to be analyzed is fluorescently labeled and hybridized to the probes on the chip. Using this technique one can determine the presence of mutations or even sequence the nucleic acid being analyzed, or one can measure expression levels of a gene of interest. A major advantage of this method is that parallel processing of many, even thousands, of probes at once can be accomplished and thereby increase the rate of analysis tremendously.

Alteration of NYX MRNA expression can be detected by any techniques known in the art. These include Northern blot analysis, PCR amplification and RNase protection. Diminished mRNA expression indicates an alteration of the wild-type NYX gene. Alteration of wild-type NYX genes can also be detected by screening for alteration of wild-type NYX protein. For example, monoclonal antibodies immunoreactive with NYX can be used to screen a tissue. Lack of cognate antigen would indicate a NYX mutation. Antibodies specific for products of mutant alleles could also be used to detect mutant NYX gene product. Such immunological assays can be done in any convenient formats known in the art. These include Western blots, immunohistochemical assays and ELISA assays. Any means for detecting an altered NYX protein can be used to detect alteration of wild-type NYX genes. Functional assays, such as protein binding determinations, can be used. In addition, assays can be used that detect NYX biochemical function, for instance, DNA binding. Finding a mutant NYX gene product indicates presence of a mutant NYX allele.

Possible consequences of NYX mutations

Fourteen different mutations have been identified in NYX, none of which are observed in chromosomes from normal individuals. In nyctalopin, there are 11 leucine-rich repeats, which are all highly conserved with respect to the consensus sequence in SLRPs, and these are flanked by cysteine clusters (see FIG. 3B) [SEQ ID NO: 2] [10]. The deletion of a portion of the oysteine cluster in the amino-terminal portion of nyctalopin appears to be responsible for complete X-linked CSNB in six families, which highlights the importance of this conserved region. The mutation that causes a stop codon on the carboxyl-terminal side of the leucine-rich repeats and another cysteine cluster, likely affects the ability of the protein to anchor in the membrane, as the protein portion on the carboxyl-terminal side of this mutation is presumed to be important for GPI anchoring nyctalopin in the cellular membrane. Mutations that replace a consensus amino acid with another amino acid axe presumed to disrupt an essential amino acid function. Mutations that result in the insertion (or deletion) of amino acids in the protein are presumed to alter the folding of the protein Missense mutations, and additions or deletions of amino acids are predicted to disrupt specific functions of intact nyctalopin and therefore may be informative as to the structure-function relationship of the protein. Such information is presumed to be useful for targeting therapy for retinal disease, either by direct action on nyctalopin or, indirectly, on proteins which interact with nyctalopin.

Construction of Full-Length cDNA Clones

Full length cDNA clones are constructed by a variety of methods known to those skilled in the art. Such methods include screening a cDNA library with a labeled DNA probe of the gene of interest, identifying overlapping cDNA clones and ligating them together into one clone that contains the entire coding region. One can also obtain a full length cDNA clone in one step from a library, obviating the need to perform intermediary ligation steps. If the 5' or 3' end only of the clone is missing, methods such as RACE (rapid amplification of cDNA ends) are used to complete the sequence, or if the full length sequence is known, PCR amplification and ligation of the fragments onto the ends of the cDNA clone may be used. The cDNA product is cloned into the vector of choice, such as a pUC™ vector or pBluescript™.

Alternatively, PCR is used to amplify the gene from a cDNA library or a cDNA preparation using a Taq Polymerase that is designed for long range PCR, such as Pfu™ or Vent™ Polymerase, and the PCR fragment is ligated into a the vector of choice. A preferred vector is PCR2.1-TOPO™ (Invitrogen). The PCR primer at the 5' end (the forward primer) is designed to contain a small ribosomal binding site. The forward primer and the PCR primer at the 3' end (the reverse primer) also contain recognition sites for extremely rare cutting restriction endonucleases, such as NotI, for cloning into the vector. If the entire cDNA sequence cannot be obtained in one step, then overlapping PCR fragments can be amplified and ligated together into a vector using methods known to those skilled in the art. PCR products are verified by DNA sequencing and restriction digestion, to ensure that they are identical in sequence to the native cDNA. After ligation into the vector, the fragments are again checked for accuracy by restriction analysis or DNA sequencing. A person skilled in the art may modify these methods as necessary, depending upon the exigencies presented in each particular step of the assembly.

Identification and Characterization of Murine NYX

The knowledge of the sequence of the human NYX gene can be used to identify and isolate the homologous gene in other mammalian species. Mouse retinal cDNA can be amplified by PCR with the primers used to amplify the human NYX gene or with other primers, such as degenerate primers, that are designed by reference to the human NYX sequence. Amplified PCR fragments, which are similar in size as the human PCR products, are sequenced and compared to the human NYX sequence. Any fragments with substantial homology (approximately 90%) to the human sequence are presumed to be portions of the murine NYX gene.

To obtain the remainder of the murine NYX sequence, mouse specific primers sets can be designed from the mouse sequence known to that point. These primers can be used to amplify the additional regions of murine NYX.

Finally, the 5' and 3' ends of the murine cDNA sequence for NYX can be obtained by 5' and 3' RACE, using the Marathon™ cDNA Amplification Kit (Clontech). These methods are well known to those skilled in the art.

Drug Screening

The invention may be useful to screen for molecules that stimulate or inhibit nyctalopin expression. Therefore, the present invention provides methods of screening for molecules having effect in cultured cells, either primary or transfected versions, by assaying for the levels of nyctalopin production by immunoprecipitation, or Western blotting and NYX transcription by Northern blotting, which are well known in the art.

EXAMPLES

The following examples are intended to illustrate but not limit the invention. While they are typical of those that might be used, other procedures known to those skilled in the art may alternatively be utilized.

Example 1—

Identification of the Genomic Region Containing the CSNB1 Locus

Twenty-four families with complete X-linked CSNB were included in this study. The diagnosis of complete X-linked CSNB in these families involved electrophysiological and psychophysical testing [18], which established the reduction or alteration of the rod pathway— and cone pathway-mediated function in the retina of these patients. The results of this type of testing on normal and affected subjects is shown in FIG. 1. FIG. 1A shows that the virtual absence of a rod response, the relative preservation of the scotopic white-flash a-wave with a severely subnormal b-wave, and the loss of the first two major photopic oscillatory potentials for thephotopic single flash. FIG. 1B shows the loss of rod sensitivity across the retina, and scattered loss of cone sensitivity. FIG. 1C the spectral sensitivity measurements, dark adapted, in a normal subject and a patient.

The preliminary genotype analysis of our families was performed as described [6,7]. Three new markers were developed based on dinucleotide repeats that were identified in large-scale DNA sequence. Primers pairs for these markers are as follows:

TABLE 1

| Polymorphism | Forward Primer | Reverse Primer |
| --- | --- | --- |
| 506B13CA1 (DXS10042) | atcacagtgccctgcctaaa (SEQ IDNO: 3) | tcccaaagtgctgggattac (SEQ IDNO: 4) |
| 200L4CA1 (DXS10044) | gaacagcaaaccaaatccaaa (SEQ ID NO: 5) | ggcctatggtaatgcctcct (SEQ ID NO: 6) |
| 169I5CA2 (DXS10045) | aaacttagctgggcatgctg (SEQ ID NO: 7) | gctgggactacatacagcaca (SEQ ID NO: 8) |

Figure 3A:
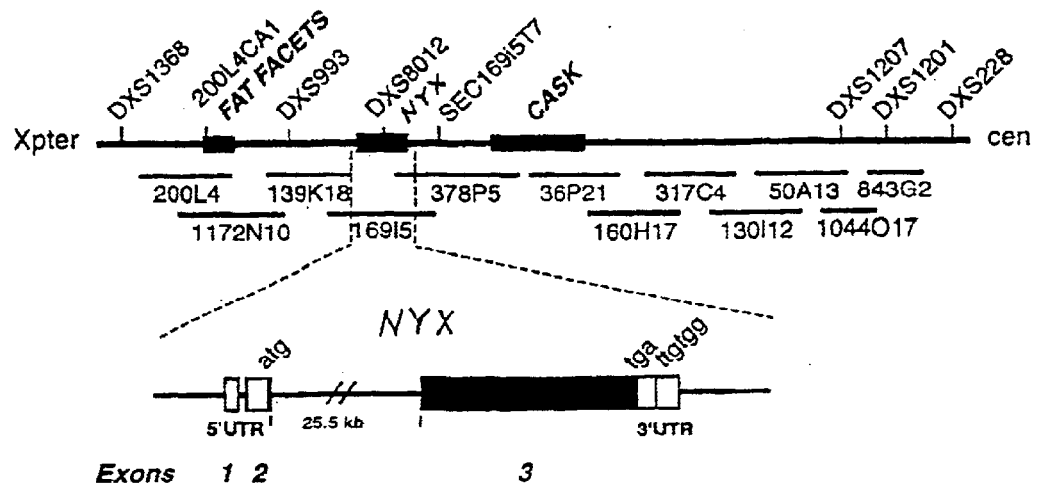
"FIG. 3A: Physical map of the CSNB1 minimal region indicating the location of overlapping BACs and PACs (short lines) and the chromosomal position of several genes in this region, including NYX The lower horizontal line demonstrates the genomic organization of NYX, showing that it is comprised of three exons, with a translation start site in the second exon, a stop codon in the third exon and a polyadenylation sequence in the 3' untranslated region.
Figure 3C:
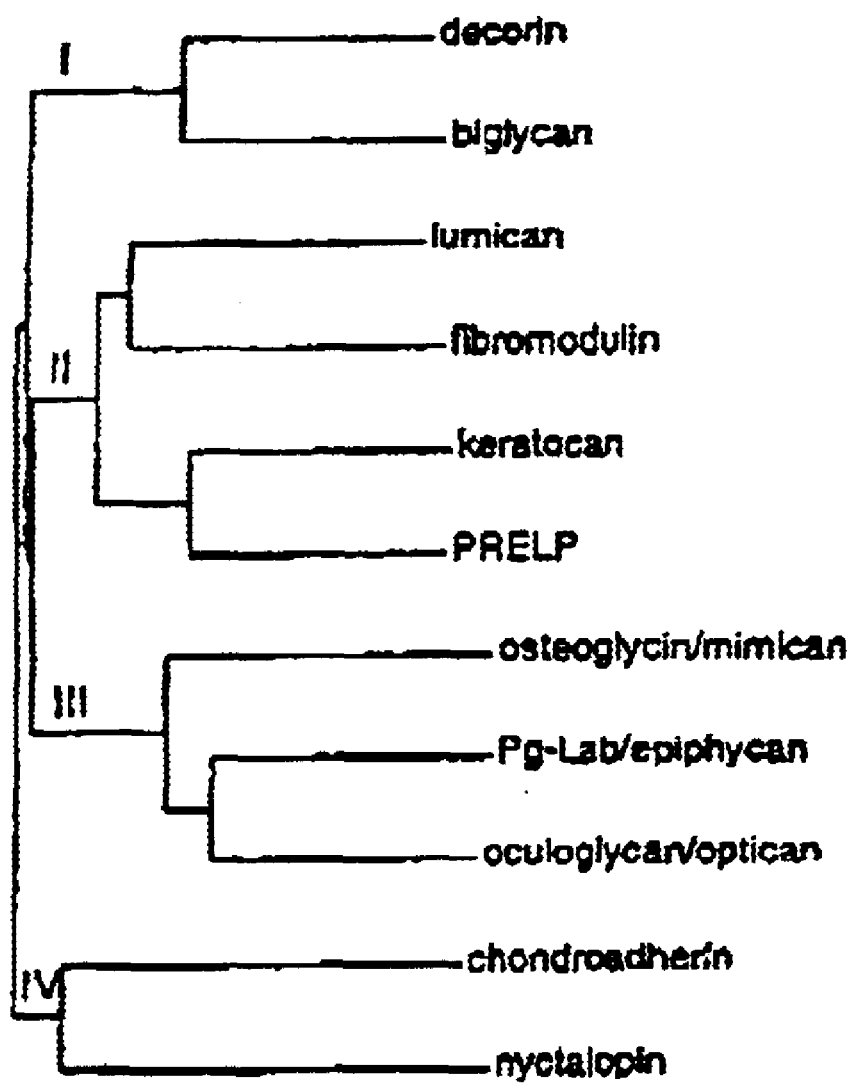
FIG. 3C: Dendogram showing the predicted relationship among members of SLRP. Chondroadherin (CHAD) and nyctalopin appear to represent a fourth class (IV) with SLRP.

Using these markers and other known markers, an analysis of selected recombinant X chromosomes in the set of families with complete X-linked CSNB enable us to moved the distal boundary of the CSNB1 minimal region from DXS556 to the interval between 200L4CA1 and DXS8012 (FIG. 2 and FIG. 3A). From further analysis, the proximal crossover previously observed in patient V:1 in family P23 [19] was limited to the interval between DXS 1207 and DXS228 (FIG. 2 and FIG. 3A).

Example 2—

Sequence of the full length NYX cDNA

To position genetic markers accurately across the CSNB1 minimal region and identify candidate genes for the CSNB1 locus, a robust physical map of the CSNB1 minimal region in Xp11.4 was developed. A subset of BAC and PAC clones from the minimal tiling path of the estimated 1.2 Mb CSNB1 minimal region is shown in FIG. 3. BAC clones 378P5, 36P21, 160H17, and 317C4, which had not been sequenced at the Sanger Center, were sequenced to between 1–2.7-fold redundancy to identify additional candidate genes. A sub-library was constructed [20] for each of the BAC clones. DNA from each BAC was isolated, randomly sheared by nebulization, and fractionated by agarose gel electrophoresis. Fragments (2–4 kb) were collected, blunt-ended, and cloned into M13mp19 using standard techniques. Random clones from each sub-library were sequenced with the aid of ABI 373 or ABI 377 sequencing machines and fluorescently labeled primers (ABI, Amersham). DNAStar™ software was used for gel trace analysis and contig assembly as well as DNA and protein alignments. DNA and protein sequences were examined against available public databases using the various Blast™ programs available through the network server at the National Center for Biotechnology Information.

The extended NYX cDNA sequence was established by sequencing of PCR and RACE products. First-strand cDNA from total human retinal RNA was used as the template for PCR. Touchdown PCR using the Failsafe™ PCR Premix Selection Kit was carried out according to the manufacturer's protocol (Epicentre Technologies). RACE was carried out using Human Retina Marathon-Ready™ cDNA (Clontech). As the GC content of exon 3 of NYX averages 72%, Advantage-GC 2™ Polymerase (Clontech) was used, and touchdown PCR for 5' RACE ( 94° C. for 30s, 72° C. for 4 min. for 5 cycles; 94° C. for 30s, 70° C. for 4 min. for 5 cycles; 94° C. for 30s, 68° C. for 4 min. for a further 25 cycles). A secondary amplification using a nested NYX specific primer was then performed using the same conditions as above. RACE and PCR products were gel purified using the Concert™ Gel Extraction kit (Life Technologies) and sequenced using the ThermoSequenase™ $^{33}$P-radiolabelled terminator cycle sequencing kit (Amersham Life Science). To establish the genomic organization of the NYX gene, the full-length cDNA sequence of NYX was compared to the genomic sequence derived from our analysis of BAC clone 378P5 and that produced by the Sanger Centre for BAC clone 16915.

BAC clone 378P5 (FIG. 3A) yielded a sequence that had partial complete homology with a 526-bp expressed sequence tag Q14392 (Accession No. AI861796). Sequence of the BAC close 378P5 in the region of homology to ESTQ14392 overlaps with the partial DNA sequence from BAC clone 16915 (FIG. 3A). GenScan and GenFinder analysis of a 20 kb portion of the genomic sequence from clone 169I5 (Sanger Center) that encompasses EST Q14392 predicted a novel open reading frame which we have designated NYX and is shown in FIG. 3A.

Example 3—

Expression of NYX in Humans

Expression of NYX was assessed by PCR amplification of a QUICK-Screen™ Human cDNA Library Panel, (Clontech) using primers spanning exon 1 to 3:

```
                                          (SEQ ID NO:9)
GXC1NF (Forward)   5'-AGGGAGTGGAGGGGACCTCAG-3';
                                          (SEQ ID NO:10)
GXC1N3R (Reverse)  5'-ACGGCACGGACGCGGTTG-3'
```

These primers generate a 755-bp product using buffer K from the Failsafe™ PCR Premix Selection Kit (Epicentre Technologies), and touchdown PCR (94° C. for 1 min., 65° C. to 55° C. over 10 cycles for 30 sec., 72° C. for 1 min. 30 sec.; then 94° C. for 1 min, 55° C. for 30 sec., 72° C. for 1 min 30 sec. for a further 29 cycles). PCR products were electrophoresed through a 1% agarose gel and visualized by ethidium bromide staining. The ubiquitously expressed EST JRL4Al was used as an amplification control. The 755-bp PCR product was detected in the retinal and kidney cDNA library (FIG. 4).

The RNA in situ hybridization method was performed as described [21–23]. Sections were hybridized with 668-bp antisense probe (from nt1557–2224 of the NYX cDNA), at a concentration of 400 ng/ml. The hybridization was done in 50% formamide, 5× sodium chloride-sodium citrate-phosphate (SSCP) and 40 mg/ml salmon sperm DNA, for 18 hr at 65° C. under Parafilm™ (American National Can, Chicago, Ill.). Two post-hybridization washes were washes were performed with 2×SSCP for a total of 30 min. at 68° C.; followed by two washes in 0.1×SSCP for a total of 1 hr at 68° C. Incubation with Fab fragments from an anti-digoxigenin antibody (1:5000) from sheep, conjugated with alkaline phosphatase (Boehringer Mannheim) for 2 hr at 22° C., followed by washes with SSCP, was used for the detection of the digoxigenin-labeled riboprobes. Precipitation of the reaction products of nitroblue tetrazolium/5-bromo-4-chloro-3-indolyl phosphate (Life Technologies) continued for 3–5 days with a daily change of substrate solution. Slides were mounted with Glycergel™ (Dako, Mississauga, Ontario, Canada). Images were obtained digitally on a Carl Zeiss Axioskop 2™ microscope with a cooled CCD camera (Diagnostic Instruments, Inc.). The images were converted to a grey scale, and the brightness and contrast were adjusted in Adobe Photoshop™.

Example 4

Mutation and segregation Analysis of NYX

Mutations were initially identified by direct DNA sequencing of PCR amplified exons from males affected with complete X-linked CSNB. PCR primers were designed to amplify from adjacent intron sequences 20–50 bp from the splice site. Additional sequencing primers internal to each exon were also used to establish total DNA sequence across an exon. A minimum of 100 control chromosomes from unrelated Caucasians were evaluated using the same or suitable techniques to test for nucleotide changes in NYX.

Genomic DNA (100–200 ng) was amplified with Platinum™ Taq polymerase (Life Technologies), in 1.5–2.5 mM $MgCl_2$, and 6% DMSO, in the supplied buffer. Touchdown PCR conditions were the same as described for establishing the nucleotide sequence of NYX (see Example 2). Purified PCR products from affected and control individuals were sequenced using ThermoSequenase™ radiolabeled terminator cycle sequencing (Amersham LIFE SCIENCE), electrophoresed on polyacrylamide gels, and visualized by autoradiography.

This analysis revealed a total of 14 different sequence alterations in NYX from 22 of the families that were studied. These mutations are summarized in FIG. 6. The observed sequence alterations segregated within families to each of the affected members and through carrier females. None of the mutations identified in patients with complete X-linked CSNB was observed in over 100 control chromosomes.

One mutation (FIG. 5A), that changed a tryptophan codon to a stop codon, was detected in patients from two large pedigrees of Hispanic origin from Costa Rica. This mutation, (designated W350X in FIG. 6) occurs on the carboxyl side of the leucine-rich repeats and cysteine clusters of nyctalopin, and is shown in FIG. 5(a).

Six other families were found to have an in-phase 24-nt deletion that results in the loss of eight amino acids— RACPAACA (see FIG. 5B). Six of these amino acids form part of a conserved cysteine-cluster on the amino-terminal side of the leucine-rich repeats, as shown in FIG. 3B [SEQ ID NO: 2]. Haplotype analysis of X chromosomes with this deletion mutation from each of the six families revealed nearly identical haplotypes, suggesting that these families share a common founder mutation. In three families, insertion mutations representing duplications of adjacent protein sequence add either six or three amino acids (FIG. 3B) [SEQ ID NO: 2].

Single-nucleotide changes in seven other families with complete X-linked CSNB are predicted to cause missense mutations. Four of these mutations change a conserved leucine to a glutamine or proline; one changes a conserved Asparagine to a Lysine and another changes a conserved Phenylalanine to a Serine (FIG. 6). FIG. 5D demonstrates one of these particular missense mutations, a T to an A which results in a Leucine to Glutamine change.

Once a nucleotide change was identified, the loss or gain of restriction sites of the PCR fragment was analyzed using DNA Strider 1.2™. For example, the G to A transition in the NYX gene in the W350X mutation destroys a FokI site. This change in restriction enzyme sites can be used for segregation analysis as shown in FIG. 5(a). PCR primers that will amplify over the region where the mutation occurs are designed as described above. The primers used were:

```
Forward:  GATTTTTCCTGGGGTGACCT   (SEQ ID NO:11)

Reverse:  GTCCAGGTCGATGGAGACC    (SEQ ID NO:12)
```

Genomic DNA samples from affected, non-affected and carrier individuals were amplified by PCR, as described above and digested with FokI. The products were separated on an agarose gel and visualized by ethidium bromide staining. In the normal NYX gene, the 916 bp PCR fragment which amplifies the region where the W350X mutation would be located, is digested by the restriction endonuclease FokI into 568- and 348-bp fragments. The PCR fragment from chromosomes of affected individuals is not digested by FokI. The PCR fragments from carrier individuals exhibit all three bands, the PCR product from the mutated gene, and the two digested bands from the normal gene.

Segregation analysis can also be performed, as shown in FIG. 5B. Primers were designed as described above to amplify over the region where the 8-amino acid deletion occurs.

The primers used were:

```
Forward: GATTTTTCCTGGGGTGACCT    (SEQ ID NO:13)

Reverse: GTCCAGGTCGATGGAGACC     (SEQ ID NO:14)
```

PCR was used to amplify the region of interest from genomic DNA of affected, non-affected and carrier individuals. The PCR products were electrophoresed through agarose gels. In FIG. 5C the gene carrying the deletion was identified in affected and carrier individuals by a 238 bp PCR fragment. The PCR fragment from normal, non-deleted chromosomes was 262 bp.

REFERENCES

The following references are cited in the application as numbers in brackets ([ ])at the relevant portion of the application. Each of these references is incorporated herein by reference.

1. Rodieck, R. W. *The First Steps in Seeing* (Sinauer, Sunderland, Mass., 1998).
2. Rattner, et al. "Molecular genetics of human retinal disease". *Annu. Rev. Genet.* 33, 85–131 (1999).
3. Carr "Congenital stationary night blindness." *Trans. Am. Ophthalmol. Soc.* 72, 448–487 (1974).
4. Miyake et al. "Congenital stationary night blindness with negative eletroretinogram." *Arch. Ophthalmol.* 104: 1013–1020 (1986).
5. Sharp, et al. "Mechanisms and sites of loss of scotopic sensitivity: a clinical analysis of congenital stationary night blindness." *Clin. Vision Sci.* 5: 217–230 (1990).
6. Boycott, et al. "Evidence for genetic heterogeneity in X-linked congenital stationary night blindness." *Am. J Hum. Genet.* 62:865–87 (1998).
7. Bech-Hansen, et al. "Localization of a gene for incomplete X-linked congenital stationary night blindness in Xp 11.23 to the interval between DXS6849 and DXS8023." *Human Genetics* 103:124–130 (1998).
8. Bech-Hansen., et al. "Loss-of-function mutations in a calcium-channel $\alpha_1$-subunit in Xp11.23 cause incomplete X-linked congenital stationary night blindness. *Nature Genet.* 19:264–267 (1998).
9. Strom, et al. (1998) "An L-type calcium-channel gene mutated in incomplete X-linked congenital stationary night blindness." *Nature Genet.* 19:260–263 (1998).
10. Hocking, et al. "Leucine-rich repeat glycoproteins of the extracellular matrix." *Matrix Biol.* 17:1–19 (1998).
11. Medof, et al. "Cell-surface engineering with GPI-anchored proteins." *FASEB J.* 10: 574–586 (1996).
12. Lewin, *"Genes" (New York, Oxford University Press;* 1997)
13. Kobe and Deisenhofer "The leucine-rich repeat: a versatile binding motif." *TIBS* 19:415–421 (1994).
14. Plaas, et al. "Identification of the keratan sulfate attachment sites on bovine fibromodulin." *J Biol. Chem.* 265: 20634–2060 (1990).
15. Nielsen, et al., "Identification of prokaryotic and eukaryotic signal peptides and prediction of their cleavage sites." *Protein Engineering* 10: 1–6 (1997).
16. Englund "The structure and biosynthesis of glycosyl phosphatidylinositol protein anchors." *Annu. Rev. Biochem* 62: 121–138 (1993).
17. Boycott, et al. "Integration of 101 DNA markers across human Xp11 using a panel of somatic cell hybrids." *Cell Cytogenet. Genet.* 76: 223–228 (1997).
18. Fishman and Sokol *"Electrophysiologic Testing in Disorders of the Retina, Optic Nerve, and Visual Pathway."* (Am. Acad. Ophthal., San Francisco, 1990)
19. Bergen, et al. *"Localization of a novel X-linked congenital stationary night blindness locus: close linkage to the RP3 type retinitis pigmentosa gene region."* *Human Molecular Genetics* 4:931–935 (1995).
20. Rowen and Koop *Automated DNA sequencing and analysis* (eds. Adams, M.D., Fields, C. & Venter, J. C.) 167–174 (Academic Press, London and San Diego, 1994).
21. Leimeister, et al., "Developmental expression patterns of mouse sRFP genes encoding members of the secreted frizzled related protein family." *Mech. Dev.* 75: 29–42 (1998).
22. Schaeren-Wiemers and Gerfin-Moser "A single protocol to detect transcripts of various types and expression levels in neural tissue and cultured cells." *Histochemistry* 100: 431–440 (1993).
23. Breitschopf, H. & Suchanek, G. *Nonradioactive in situ hybridization application manual.* pp. 136–140 (Boehringer Mannheim, Mannheim, Germany, 1996).
24. Bech-Hansen, N. T. et al. "Mutations in NYX, encoding the leucine-rich proteoglycan nyctalopin, cause X-linked complete congenital staionary night blindness." *Nature Genetics* 26: 319–323 (November, 2000)

What is claimed is:

1. An isolated or recombinant DNA molecule encoding the amino acid sequence of SEQ ID NO: 2.

2. The DNA molecule of claim 1 comprising a nucleotide sequence corresponding to SEQ ID NO: 1.

3. An isolated or recombinant polynucleotide comprising a nucleotide sequence corresponding to SEQ ID NO: 1.

4. The polynucleotide of claim 3 wherein said polynucleotide is selected from the group comprising:

(a) RNA;
(b) cDNA; and
(c) genomic DNA.

5. An expression vector comprising one of the DNAS or polynucleotides of claims 1, 2, 3 or 4.

6. A cultured cell comprising the expression vector of claim 5.

* * * * *